(12) United States Patent
Pavani

(10) Patent No.: US 9,612,273 B2
(45) Date of Patent: Apr. 4, 2017

(54) DISTRIBUTED WAFER INSPECTION

(71) Applicant: Sri Rama Prasanna Pavani, Palo Alto, CA (US)

(72) Inventor: Sri Rama Prasanna Pavani, Palo Alto, CA (US)

(73) Assignee: Exnodes Inc., Palo Alto, CA (US)

( * ) Notice: Subject to any disclaimer, the term of this patent is extended or adjusted under 35 U.S.C. 154(b) by 257 days.

(21) Appl. No.: 14/556,058

(22) Filed: Nov. 28, 2014

(65) Prior Publication Data

US 2016/0154052 A1 Jun. 2, 2016

(51) Int. Cl.
*G01R 31/26* (2014.01)
*G01N 33/00* (2006.01)

(52) U.S. Cl.
CPC ............. *G01R 31/26* (2013.01); *G01N 33/00* (2013.01); *G01N 2033/0095* (2013.01)

(58) Field of Classification Search
None
See application file for complete search history.

(56) References Cited

U.S. PATENT DOCUMENTS

| | | |
|---|---|---|
| 5,129,009 A | 7/1992 | Lebeau |
| 6,370,487 B1* | 4/2002 | Dorough ............ G02B 21/365 348/E7.086 |
| 6,580,087 B1 | 6/2003 | Suzuki et al. |
| 6,738,506 B2 | 5/2004 | Miller et al. |

(Continued)

*Primary Examiner* — Kenny Lin

(57) ABSTRACT

A system and method for inspecting a surface with cloud based processing, comprising: generating surface data by inspecting a surface; transferring said surface data from a client to a cloud, wherein said cloud comprises multiple interconnected computing nodes that are remotely located from said client; computing surface properties using said surface data on said cloud; generating surface analytics from said surface properties and a prior information set, with said prior information set comprising surface properties previously stored in said cloud; and transferring said surface properties and said surface analytics from said cloud to said client, whereby said surface properties and said surface analytics are generated with processing power, memory, and storage that are scalable, reliable, and upgradable on demand. A method for improving production yield of an article with cloud based processing, comprising: storing said process information in said cloud; transferring functional results to said cloud, with said functional results comprising identifying information of said articles that have failed a functional test and identifying information of said articles that have passed said functional test; generating a probable cause list from said process information in said cloud, wherein said probable cause list comprises a list of differences between said process information of one or more failed articles and said process information of one or more passed articles; and generating a root cause list from said probable cause list in said cloud, wherein said root cause list comprises process information responsible for failure in failed articles, whereby root causes of failures are analytically determined with processing power, memory, and storage that are scalable, reliable, and upgradable on demand.

20 Claims, 14 Drawing Sheets

(56) References Cited

U.S. PATENT DOCUMENTS

| | | | | |
|---|---|---|---|---|
| 6,957,154 | B2* | 10/2005 | Steele | G01N 27/002 |
| | | | | 134/1.3 |
| 7,253,766 | B2* | 8/2007 | Foote | G01S 13/003 |
| | | | | 342/179 |
| 7,697,727 | B2* | 4/2010 | Xu | G01C 7/04 |
| | | | | 382/108 |
| 8,126,255 | B2 | 2/2012 | Bhaskar et al. | |
| 8,618,485 | B1* | 12/2013 | Lockhart | G01N 15/06 |
| | | | | 250/341.1 |
| 8,874,266 | B1* | 10/2014 | Francis, Jr. | G05B 23/0221 |
| | | | | 700/247 |
| 2002/0005943 | A1* | 1/2002 | Voinalovich | G01N 21/9501 |
| | | | | 356/73 |
| 2002/0183963 | A1* | 12/2002 | Kocimski | B24B 37/042 |
| | | | | 702/167 |
| 2004/0108999 | A1* | 6/2004 | Martin | G06T 17/20 |
| | | | | 345/423 |
| 2006/0009942 | A1* | 1/2006 | Keck | G06F 17/30554 |
| | | | | 702/122 |
| 2007/0115483 | A1* | 5/2007 | Oak | G01B 11/303 |
| | | | | 356/600 |
| 2009/0073440 | A1* | 3/2009 | Tiemeyer | G01N 21/9501 |
| | | | | 356/338 |
| 2009/0171605 | A1* | 7/2009 | Thomson | G01N 21/95607 |
| | | | | 702/81 |

* cited by examiner

| Features | | | | | | | | | | |
|---|---|---|---|---|---|---|---|---|---|---|
| X Position | Y Position | Z Position | X Size | Y Size | Z Size | Equivalent Size | Orientation | Type | Index | Absorption |
| : | : | : | : | : | : | : | : | : | : | : |

| Layer | | | | |
|---|---|---|---|---|
| Average thickness | : | | | |
| Index | : | | | |
| Absorption | : | | | |
| Haze | : | | | |
| Correlation | : | | | |
| Deviation | : | | | |
| Shape | X Position | Y Position | Sag | |
| | : | : | : | |

30 ← (Features)
31 ← (Layer)

FIG. 2

| Features | Min | Max |
|---|---|---|
| X Position | .. | .. |
| Y Position | .. | .. |
| Z Position | .. | .. |
| X Size | .. | .. |
| Y Size | .. | .. |
| Z Size | .. | .. |
| Equivalent Size | .. | .. |
| Orientation | .. | .. |
| Type | .. | .. |
| Index | .. | .. |
| Absorption | .. | .. |

| Layer | Min | Max |
|---|---|---|
| Thickness | .. | .. |
| Index | .. | .. |
| Absorption | .. | .. |
| Haze | .. | .. |
| Correlation | .. | .. |
| Deviation | .. | .. |

FIG. 4

DISTRIBUTED WAFER INSPECTION

FIELD OF THE INVENTION

This invention relates generally to wafer inspection and more particularly to using cloud based processing for inspecting a surface and improving production yield.

BACKGROUND

Integrated circuits (ICs) are sophisticated semiconductor components that provide processing, memory, and storage capabilities to modern electronic devices. Advances in IC fabrication have enabled a wide range of devices from wearable devices to surgical robots. ICs comprise a number of layers of intricate sub-micrometer scale structures that implement rudimentary logic and memory cells. Fabrication of ICs comprise hundreds of process steps, such as implantation, deposition, lithography, etching, polishing, and packaging, that transform bare semiconductor wafers into ICs. Upon fabrication, ICs are tested to check if their functional performance meets target specifications. The ratio of the number of ICs that meet target specifications to the total number of fabricated ICs is known as production yield. Since yield has a direct impact on the cost of an IC, maximizing yield is an important activity in semiconductor fabrication.

Maximizing yield, however, is a challenging task because of the exhaustive number and complexity of steps involved in IC fabrication. To facilitate the task, wafer inspection and metrology systems are employed to inspect for abnormalities after each significant process step. For example, a wafer inspection system may be used for detecting defects; a wafer review system may be used for resolving and identifying defects; a wafer metrology system may be used for measuring the properties of one or more films on a wafer; and a wafer shape system may be used for measuring the shape of a wafer. Abnormalities or defects detected by wafer inspection and metrology systems are monitored closely. When the abnormalities or defects become intolerable, process steps are adjusted in an effort to bring them back to tolerable levels.

Advances in semiconductor fabrication such as node scaling, 3D transistors, 450 mm wafer size, and the use of new materials have brought upon increased challenges to wafer inspection and metrology systems. Node scaling refers to the trend of decreasing size of components inside ICs. Node scaling and increasing wafer size have allowed ICs to improve their performance (increased speed, reduced power, increased memory capacity, increased memory bandwidth) while simultaneously reducing their cost. However, wafer inspection systems have not been able to effectively meet the challenges imposed by advances in semiconductor fabrication. For example, while the smallest IC structures shrank from 130 nm to 14 nm (over 9× reduction) over the last decade, defect sensitivity of optical wafer inspection systems improved at a substantially slower rate from 50 nm to 20 nm (2.5× reduction) in the same time period. Since the size of yield affecting defects decreases at the same rate as node scaling, the slower rate of improvement in defect sensitivity has resulted in a negative impact on yield.

Wafer inspection systems capture a large amount of data to inspect a wafer. For instance, in a typical wafer inspection system, a micrometer scale laser beam is scanned over a wafer as large as few hundred millimeters. Light scattered from each point on the wafer is captured. Wafer size can be as large as 450 mm, and the number of points can be over a billion. Typical wafer inspection systems exhibit defect sensitivity of about 20 nm. This means that a 20 nm size spherical particle made out of silica or polystyrene latex can be reliably detected. A 20 nm particle has a surface area that is over 100 trillion times smaller than the surface area of a 450 mm wafer. Accordingly, detecting such small defects reliably requires high-performance computing systems that operate on a large quantity of data.

A traditional wafer inspection system employs a high performance computer that is collocated with an inspection module. The computer has finite processing, memory, and storage capabilities. The computer executes a software application to process the above mentioned large quantity of data. Accordingly, computing is centralized in a traditional wafer inspection system. Such centralization increases the risk of a single point of failure. That is, any malfunction in software, processor, memory, or storage could make the wafer inspection system non-functional. Therefore, computing infrastructure in traditional wafer inspection systems is not reliable. Further, the computing infrastructure in a traditional inspection system is not scalable. That is, the processing, memory, and storage capabilities cannot be arbitrarily expanded in a traditional wafer inspection system. Furthermore, the computing infrastructure is not upgradable or downgradable on demand. That is, the processing, memory, and storage capabilities cannot be readily reconfigured in a traditional wafer inspection system. The lack of reliability, scalability, and upgradability of computing infrastructure in traditional wafer inspection systems restricts traditional wafer inspection systems from using sophisticated data processing techniques.

Although traditional wafer inspection and metrology systems detect defects and abnormalities, they do not have the capability to classify yield affecting defects from other harmless defects. On the one hand, this may lead to negligence of root-cause analysis for yield affecting defects. On the other hand, this may also lead to needless root-cause analysis for harmless defects. Further, the information generated by traditional wafer inspection techniques are restricted to data obtained from a wafer under inspection. As a result, analytical trends about yield-affecting wafer characteristics are unavailable.

Maximizing yield involves using information provided by wafer inspection and metrology systems to identify and correct the root cause of abnormalities or defects that are responsible for rendering an IC non-functional. However, doing so is a formidable challenge because of the exhaustive range of failure modes in IC fabrication. In other words, the challenge is to identify abnormalities or defects responsible for the failure of an IC from hundreds of process steps. Traditional wafer inspection techniques do not have the capability to analytically identify the root cause of IC failures.

Traditional wafer inspection suffers from a number of problems, including: a) lack of a reliable computing infrastructure; b) lack of a scalable computing infrastructure; c) lack of an upgradable computing infrastructure; d) inability to classify yield affecting defects/abnormalities from harmless defects/abnormalities; e) inability to generate trends about yield-affecting defects/abnormalities; and f) inability to identify root cause of yield affecting defects/abnormalities.

Accordingly, there is a need for an improved wafer inspection system and a method that has a reliable, scalable, and upgradable computing infrastructure; has the ability to classify yield affecting defects/abnormalities from harmless defects/abnormalities; has the ability to generate trends about yield-affecting defects/abnormalities; and has the ability to identify root cause of yield affecting defects/abnormalities.

SUMMARY

The invention is a system and method for inspecting a surface with cloud based processing, and a method for improving production yield of an article with cloud based processing.

In some embodiments, the invention is a system for inspecting a surface with cloud based processing, comprising: an inspection module to generate surface data by inspecting a surface, with said inspection module connected to a client; a communication pathway configured to: transfer said surface data from said client to a cloud, wherein said cloud comprises multiple interconnected computing nodes that are remotely located from said client; transfer surface properties and surface analytics from said cloud to said client; and a processor configured to: compute said surface properties using said surface data, with said processor located in said cloud; generate said surface analytics from said surface properties and a prior information set, with said prior information set comprising surface properties previously stored in said cloud, whereby said surface properties and said surface analytics are generated with processing power, memory, and storage that are scalable, reliable, and upgradable on demand.

In some embodiments, the invention is a method for inspecting a surface with cloud based processing, comprising: generating surface data by inspecting a surface; transferring said surface data from a client to a cloud, wherein said cloud comprises multiple interconnected computing nodes that are remotely located from said client; computing surface properties using said surface data on said cloud; generating surface analytics from said surface properties and a prior information set, with said prior information set comprising surface properties previously stored in said cloud; and transferring said surface properties and said surface analytics from said cloud to said client, whereby said surface properties and said surface analytics are generated with processing power, memory, and storage that are scalable, reliable, and upgradable on demand.

In some embodiments, the invention is a method for improving production yield of an article with cloud based processing, comprising: storing said process information in said cloud; transferring functional results to said cloud, with said functional results comprising identifying information of said articles that have failed a functional test and identifying information of said articles that have passed said functional test; generating a probable cause list from said process information in said cloud, wherein said probable cause list comprises a list of differences between said process information of one or more failed articles and said process information of one or more passed articles; and generating a root cause list from said probable cause list in said cloud, wherein said root cause list comprises process information responsible for failure in failed articles, whereby root causes of failures are analytically determined with processing power, memory, and storage that are scalable, reliable, and upgradable on demand.

BRIEF DESCRIPTION OF THE DRAWINGS

FIG. 2 illustrates surface properties computed using surface data, in accordance with the invention.

FIG. 4 illustrates a collection of tolerable values of surface properties, in accordance with the invention.

DETAILED DESCRIPTION OF THE PREFERRED EMBODIMENTS

Figure 1:
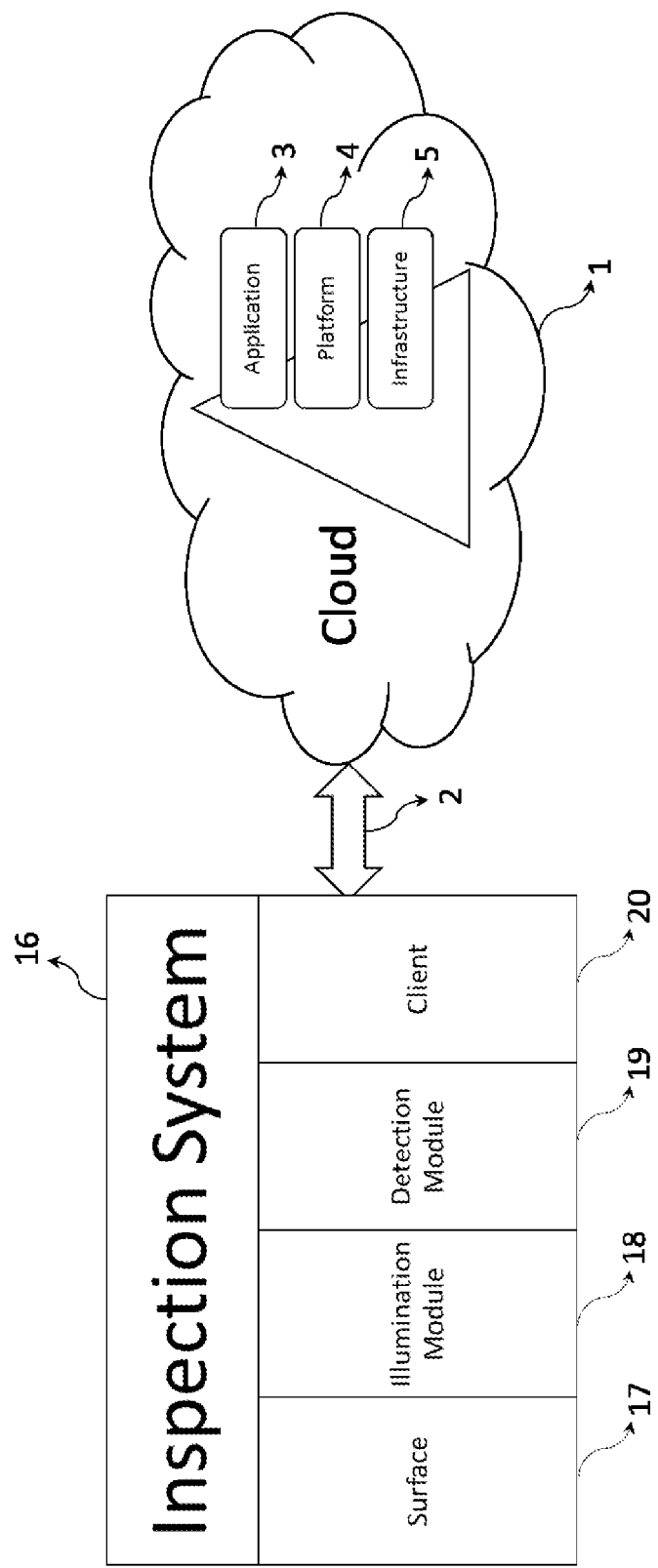
FIG. 1 shows an inspection system with cloud based processing, in accordance with the invention.

FIG. 1 shows an inspection system 16 with cloud based processing, in accordance with the invention. The inspection system 16 inspects a surface 17 with an illumination module 18 and a detection module 19. The surface data captured by the inspection system 16 is transferred to a cloud 1 with a client 20. In some embodiments, the surface data is stored in cloud 1. A bidirectional communication pathway 2 facilitates communication between the inspection system 16 and cloud 1. The cloud 1 processes surface data received from inspection system 16 to generate surface properties. The cloud also generates surface analytics of surface properties. The surface properties and surface analytics generated in the cloud are transferred to the inspection system using the communication pathway 2.

In some embodiments, the inspection system comprises surface handling equipment such as a chuck and surface handling robots. In some embodiments, the surface 17 is a semiconductor wafer. In other embodiments, surface 17 is a substrate with paths having electrical conductivity. The illumination module 18 illuminates surface 17 with an electromagnetic radiation. Surface 17 scatters incident electromagnetic radiation. Scattering includes transmission and reflection. In some embodiments, the scattered radiation encodes information on features present on the surface. In some embodiments, the scattered radiation encodes information on surface properties such as thickness and shape of surface. In some embodiments, the scattered radiation encodes information on surface roughness. The detection module 19 captures scattered radiation and generates surface data. In some embodiments, the surface data comprises a digital representation of an electromagnetic radiation scattered from surface 17. In some embodiments, detection module 19 comprises imaging optics to collect scattered radiation. In some embodiments, the detection module 19 uses one or more photodetectors such as photo multiplier tubes, photodiodes, or image sensors to capture the scattered electromagnetic radiation. The surface data from detection module 19 passes to a client 20. The client 20 comprises an interface to connect to a communication pathway 2. For example, the thin client 20 may comprise a network interface such as an Ethernet port, WiFi port, or a high speed network port. In some embodiments, the thin client 20 compresses the surface data before transmitting through the communication pathway 2. Accordingly, in some embodiments, a processor is configured to compress surface data in client 20 to generate a compressed surface data, and a processor configured to decompress compressed surface data in cloud 1 to retrieve surface data. In some embodiments, the client packetizes surface data in accordance with the internet protocol suite. In some embodiments, the internet protocol suite comprises protocols operating in application layer, transport layer, internet layer, and a link layer.

Cloud 1 is a network of interconnected computing nodes. In some embodiments, cloud 1 comprises an infrastructure layer 5, a platform layer 4, and an application layer 3. The infrastructure layer 5 comprises processors, memory, storage, and network interfaces. The application layer 3 comprises software applications that generate surface properties and surface analytics from surface data. In some embodiments, surface properties comprise position and size of features located on surface 17. In some embodiments, surface properties comprise shape and thickness. The platform layer 4 comprises software such as operating system, database, and development tools that facilitate the operation of applications in the application layer 3 on the infrastructure layer 5. In some embodiments, the software applications on the application layer 3 may be deployed as a software as a service model. In other applications, the platform layer 4 may be deployed as a platform as a service model. In some embodiments, the infrastructure layer 5 may be deployed as an infrastructure as a service model. In some embodiments, cloud 1 is a private cloud, which is dedicated to one or more semiconductor fabs. In other embodiments, cloud 1 is a public cloud, which is shared between multiple diverse cloud users. In some embodiments, cloud 1 is a hybrid cloud, comprising both private and public clouds.

The interconnected computing nodes present in cloud 1 can be dynamically configured. In some embodiments, instances of a cloud application computing surface properties and surface analytics are executed in multiple computing nodes simultaneously. Accordingly, if one computing node fails due to hardware or software failures, the other interconnected computing nodes continue to compute surface properties and surface analytics. Furthermore, the other interconnected computing nodes recognize the failure of the failed computing node and automatically create a new computing node instance to compute surface properties and surface analytics. Therefore, computing on the cloud is reliable. Each computing node comprises processor, memory, and storage. The processing, memory, and storage capabilities can be scaled by increasing the number of computing nodes. Additionally, such a scaling upgrade may be performed elastically without the need for shutting down an inspection system. Accordingly, surface properties and surface analytics are generated with processing power, memory, and storage that are scalable, reliable, and upgradable on demand.

FIG. 2 illustrates surface properties computed using surface data, in accordance with the invention. In some embodiments, surface properties comprise information on features 30 present on the surface. Features include defects such as particles, process induced defects, crystalline originated pits, residues, and scratches. Features may also include other fabricated structures on the surface. In some embodiments, surface properties comprise information on layers 31 present on a surface. Layers refer to films on or inside the surface. For example, layers include epitaxial layers, insulating layers, conducting layers, metal layers, and dielectric layers. Surface properties are computed in a cloud application using surface data received from an inspection system. In some embodiments, a prior information set comprising models of features and layers may be used together with surface data to compute surface properties.

In some embodiments, information on features 30 includes position of features in X and Y dimensions. Position of a feature refers to the location of the feature on the surface under inspection. In some embodiments, information on features 30 includes position of features in the Z dimension. In some embodiments, information on features 30 includes size of features in X and Y dimensions. Size of a feature along a dimension refers to the width of the feature along the dimension. In some embodiments, information on features 30 includes size of features in Z dimension. In some embodiments, information on features 30 includes the equivalent size of a feature. Equivalent size of a feature refers to the size of a spherical particle having substantially similar scattering intensity as the feature. In some embodiments, information on features 30 includes information on the orientation of the feature. Orientation of a feature refers to the direction of the major axis of a feature. In some embodiments, information on features 30 includes information on type of feature. Type refers to a category assigned to a feature based on the properties of the feature such as the shape and size. For example, type of a feature may be a particle, process induced defect, residue, crystalline originated pit, or a scratch. In some embodiments, information on features 30 includes the refractive index of the feature. In some embodiments, information on features 30 includes the absorption coefficient of the feature.

In some embodiments, information on layer 31 includes the shape of a surface layer. Shape of a surface layer refers to the sag of the surface layer at a variety of X and Y positions. In some embodiments, information on layer 31 includes the average thickness of a surface layer. In some embodiments, information on layer 31 includes the refractive index of the surface layer. In some embodiments, information on layer 31 includes the absorption coefficient of the surface layer. In some embodiments, information on layer 31 includes the haze of the surface. Haze refers to scattered electromagnetic radiation due to the roughness of the surface. Haze increases as the standard deviation of roughness increases, where standard deviation quantifies the deviation of surface height with respect to an average value. In some embodiments, standard deviation is the width of the height distribution of surface roughness. Haze also increases as the correlation width of the autocovariance function of surface roughness increases. In some embodiments, information on layer 31 includes the correlation width of the surface. In some embodiments, information on layer 31 includes the standard deviation of the height distribution of the surface.

Features of a surface may be detected by using wafer inspection systems. In some embodiments, dark field inspection systems may be used to illuminate a surface with an electromagnetic radiation and to capture scattered radiation from the surface. Feature positions may then be determined by searching for captured radiation that is substantially higher than the background. In other embodiments, wafer inspection systems may be used to capture two dimensional images of a region of surface. Features may be detected by comparing an image of a region with an image of another region or by comparing an image of a region with a model of the region. In this case, the differences obtained through comparison are considered as features. In some embodiments an electron microscope based review system is used to capture a high resolution image of features. The position of a feature is estimated from the intensity of scattered radiation captured by the wafer inspection system. In some embodiments, the intensity of scattered radiation is compared with a scattering model of a feature to estimate the position of the feature. The size of a feature may be estimated by measuring the width of feature pixels along X, Y, and Z dimensions. The equivalent size of the feature may be estimated from the overall intensity scattered by the feature. The orientation and type of the feature may be estimated by analyzing the shape of the intensity pattern of scattered intensity captured from the feature. In some embodiments, images of features showing shapes of known features may be stored in the cloud. Such images with known shapes may then be compared with the scattered radiation captured from wafer inspection systems to determine the orientation and type of the feature generating the scattered radiation. In some embodiments, refractive index is determined from a lookup table having a previously established correspondence between shape and refractive index. Similarly, in some embodiments, absorption coefficient is determined from a lookup table having a previously established correspondence between shape and absorption coefficient.

A surface may comprise multiple features. Information on position, size, orientation, type, index, and absorption corresponding to one or more features may be listed under feature properties 30. In some embodiments, feature properties may comprise a subset of properties listed in 30. For example, feature properties may comprise X position, Y position, and equivalent size. In some embodiments, feature properties may comprise other properties related to a feature, such as conductivity. Therefore, the feature information shown in 30 should be considered as an exemplary list of feature properties.

The shape of a surface layer may be measured with interferometry, where the wavefront from the surface layer is interfered with a known reference wavefront to produce interference fringes. By analyzing the interference fringes, the wavefront from the surface is estimated. Wavefront from the surface is related to the shape of the wafer. In some embodiments, shape is calculated from wavefront as, $S(x,y)=W(x,y)\lambda/2\pi n$, where $S(x,y)$ is the surface shape, $W(x,y)$ is the difference between the wavefront of a surface and a plane wavefront, $\lambda$ is the wavelength of the electromagnetic radiation used to produce the interference fringes, and n is the refractive index of the medium comprising the surface. Average thickness refers to the average thickness of a layer within a two dimensional region of interest. In some embodiments, thickness of a layer may be measured using ellipsometry. Here, the change in polarization of an electromagnetic radiation upon reflection from the surface is measured. This change in polarization may then be transformed into layer thickness. In some embodiments, the Drude equation may be used to relate layer thickness to the ratio of reflected p polarization to reflected s polarization components. In some embodiments, thickness may also be measured using interferometry. Ellipsometry may be used to measure refractive index. Refractive index and absorption coefficient may be measured with interferometry. Absorption coefficient may be measured with ellipsometry or reflectometery. Haze may be measured by capturing scattered radiation from a surface region without feature. In some embodiments, correlation and deviation may be deduced from total integrated scatter from the surface. In other embodiments, an atomic force microscope may be used to capture high resolution images of surface roughness. Correlation and deviation of surface roughness may be computed from the images captured by atomic force microscopes.

In some embodiments, layer properties may comprise a subset of properties listed in 31. For example, layer properties may comprise thickness and haze. In some embodiments, layer properties may comprise other properties related to a layer, such as conductivity. Therefore, the layer information shown in 31 should be considered as an exemplary list of layer properties.

Figure 3:
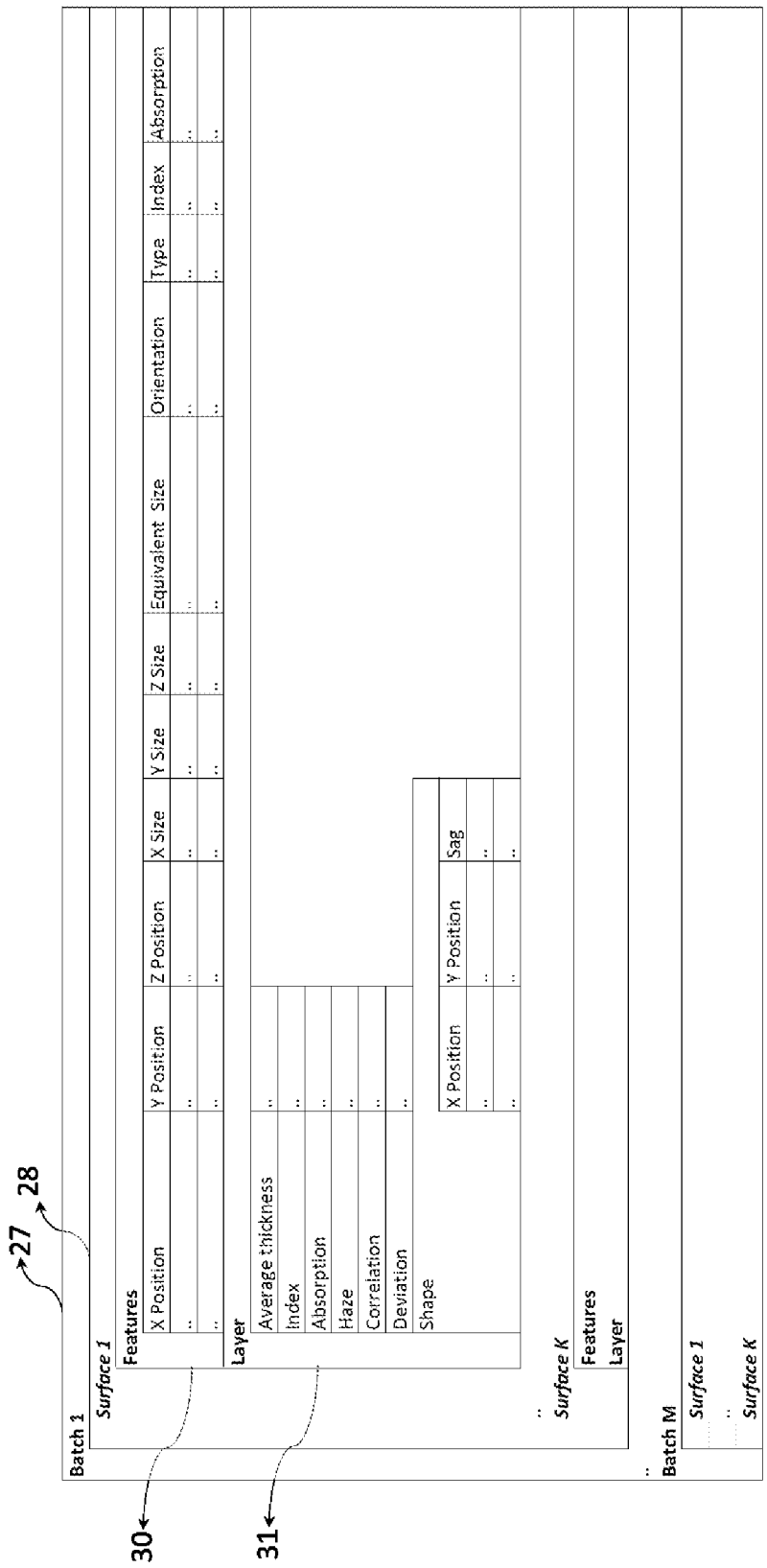
FIG. 3 illustrates a prior information set stored in cloud, in accordance with the invention.

FIG. 3 illustrates a prior information set 27 stored in cloud, in accordance with the invention. The prior information set 27 comprises a collection of surface properties from two or more surfaces. The prior information set 27 comprises prior information from a number of batches. Each batch 28 comprises prior information from a number of surfaces. Each surface comprises information on features 30 and information on layer 31. Accordingly, prior information set comprises surface information from multiple surfaces. The prior information set may be used to compute analytics on one or more surface properties. For example, variation in the value of a surface property across a number of surfaces and across number of batches may be computed using the prior information set 27. In some embodiments, the prior information set is stored in a database located in the cloud. In some embodiments, prior information set 27 is built by storing surface data and surface properties in the cloud after a surface is inspected by a wafer inspection or metrology system.

FIG. 4 illustrates a collection of tolerable values of surface properties, in accordance with the invention. In some embodiments, the prior information set may also comprise a collection of minimum and maximum values for one or more surface properties. An exemplary collection of tolerable values 58 shows minimum and maximum tolerable values for a number of feature and surface properties. In some embodiments, minimum and maximum values for feature properties are listed. In some embodiments, minimum and maximum values for layer properties are listed. Feature properties refer to X position, Y position, Z position, X size, Y size, Z size, equivalent size, orientation, type, index, and absorption. Layer properties refer to thickness, index, absorption, haze, correlation, and deviation. In some embodiments, feature properties may comprise a subset of properties listed in 58. For example, feature properties may comprise X position, Y position, and equivalent size. In some embodiments, feature properties may comprise other properties related to feature, such as conductivity. Therefore, the feature information shown in 58 should be considered as an exemplary list of feature properties. In some embodiments, layer properties may comprise a subset of properties listed in 58. For example, layer properties may comprise thickness and haze. In some embodiments, layer properties may comprise other properties related to a layer, such as conductivity. Therefore, the layer information shown in 58 should be considered as an exemplary list of layer properties.

Figure 5:
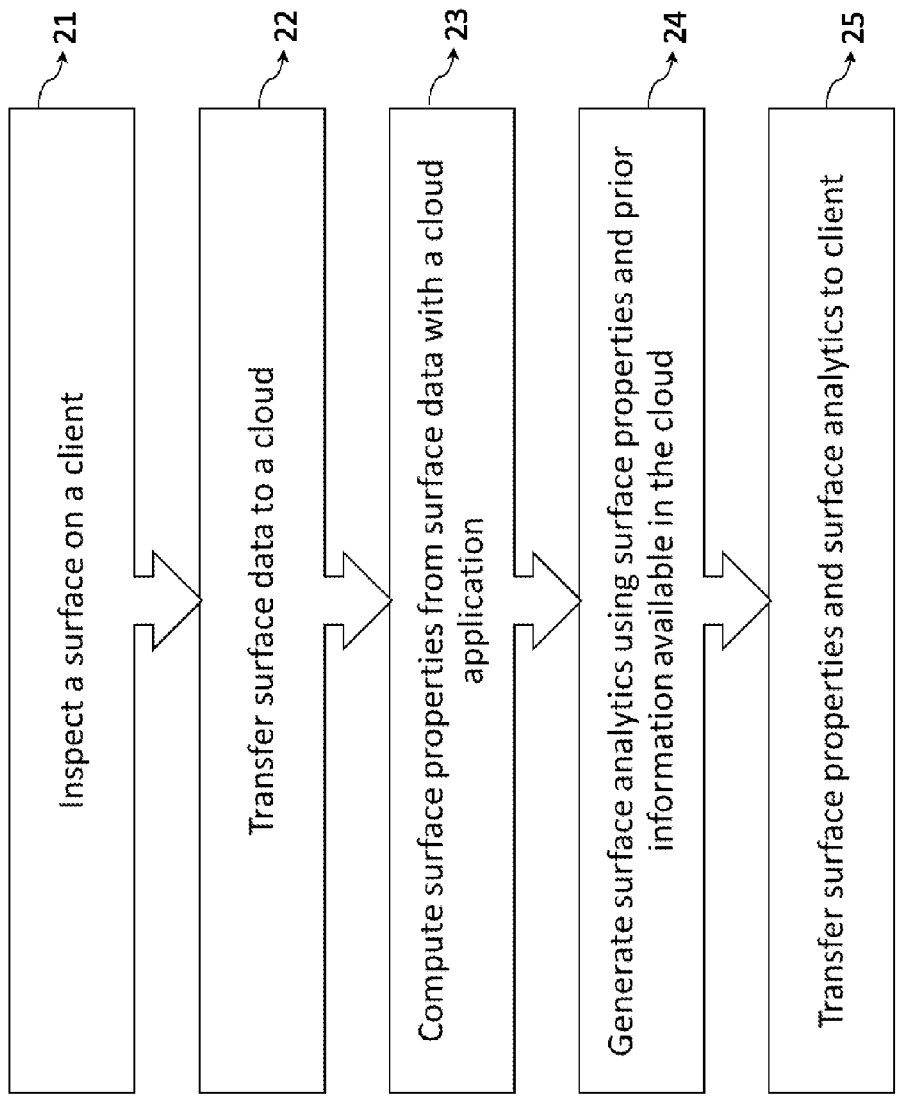
FIG. 5 illustrates an exemplary flow chart for computing surface properties and generating surface analytics using cloud based processing, in accordance with the invention.

FIG. 5 illustrates an exemplary flow chart for computing surface properties and generating surface analytics using cloud based processing, in accordance with the invention. In block 21, a surface is inspected on a client. Surface data is generated during inspection. In some embodiments, the surface data is compressed to reduce data size. In some embodiments, a wafer inspection system is used for inspection. In some embodiments, a wafer review system is used for inspection. In other embodiments, a wafer shape system is used for inspection. In some embodiments, ellipsometer, interferometer, or a reflectometry system is used for inspection. The inspection system is connected to a client. The client packetizes surface data according to the internet protocol suite. In block 22, surface data from client is transferred to the cloud using a communication pathway. Communication pathway refers to a channel through which client data is communicated to the cloud. The packetized data from client is sent from the application layer of the internet protocol suite to the transport layer, internet layer, and to the link layer. Each data packet comprises a destination address, which points to the cloud. Transmission from client may be accomplished with wired or wireless network interfaces on the client. In some embodiments, transmission control protocol is used in the transport layer. In other embodiments, user datagram protocol is used in the transport layer. In some embodiments, internet protocol is used in the internet layer. In some embodiments, real time streaming protocol is used in the application layer. In other embodiments, FTP is used in the application layer. In some embodiments, a twisted pair copper cable is used to physically transfer data from link layer. In some embodiments, an optical fiber is used to physically transfer data from link layer. In some embodiments, a coax cable is used to physically transfer data from link layer. In some embodiments, data is transferred wirelessly. For example, IEEE 802.11 protocol may be used to wirelessly communicate surface data. In some embodiments, the communication pathway comprises routers that route surface data from client to the cloud.

In block 23, surface properties are computed from surface data with a cloud application. In some embodiments, a cloud application retrieves surface data with an internet protocol suite on the cloud. That is, surface data is reconstructed by link layer, internet layer, transport layer, and finally by the application layer. In some embodiments, the surface data is decompressed to its original size. The surface data received from the client comprises identifying information about the client. The cloud application is configured to use this identifying information to determine the surface properties to be retrieved from surface data. For example, if the client is a wafer inspection system, feature properties and haze may be estimated from the surface data. Alternatively, if the client is a wafer shape system, wafer shape information is retrieved from surface data. And if the client is an ellipsometer, surface layer thickness and refractive index may be estimated from surface data.

In the case of a wafer inspection client, surface data comprises digitized version of scattered radiation from various points of the surface. Features may be detected by searching for pixels having substantially different values from their local neighborhood. Thresholds may be used to separate background pixels from feature pixels. The value of the threshold is adaptively selected based on the background value in a local neighborhood. Accordingly, features in regions having different background levels may be detected. The position of a feature may be estimated by localizing the position of feature pixels. In some embodiments, the intensity of feature pixels may be fitted to a model to estimate the position of a feature. In other embodiments, a point on or inside a feature may be chosen as the position of the feature. For instance, the centroid of feature pixels may be chosen as the position of the feature. In some embodiments, the size of feature may be estimated from the width of feature pixels from an image in which the feature is resolved. In other embodiments, an equivalent size of a feature is estimated from the intensity of pixels in the feature region. Since scattering intensity increases with size, a look up table may be generated by calibrating scattering intensities of features with known sizes. The size of an unknown feature may then be estimated from the look up table using the intensity of the feature. The orientation and type of the feature may be estimated by analyzing the shape of the intensity pattern of scattered intensity captured from the feature. For facilitating this analysis, images of features showing shapes of known features may be stored in the cloud. Such images with known shapes may then be compared with the scattered radiation captured from the wafer inspection systems to determine the orientation and type of a feature. For example, the orientation and type of an image that exhibits the closest match to a captured scattered radiation is determined as the orientation and type of the feature generating the scattered radiation. In some embodiments, refractive index is determined from a lookup table having a previously established correspondence between shape and refractive index. Similarly, in some embodiments, absorption coefficient is determined from a lookup table having a previously established correspondence between shape and absorption coefficient In the case of a wafer shape system, the wavefront from the surface is estimated by analyzing the interference fringes captured in surface data. Wavefront from the surface is related to the shape of the wafer. In some embodiments, shape is calculated from wavefront as, $S(x,y)=W(x,y)\lambda/2\pi n$, where $S(x,y)$ is the surface shape, $W(x,y)$ is the difference between the wavefront of a surface and a plane wavefront, $\lambda$ is the wavelength of the electromagnetic radiation used to produce the interference fringes, and n is the refractive index of the medium comprising the surface. In the case of an ellipsometer, the Drude equation may be used to compute layer thickness from the ratio of reflected p polarization to reflected s polarization components. In some embodiments, thickness may be measured using interferometry. Alternatively, the Drude equation may be used to compute refractive index from the ratio of reflected p polarization to reflected s polarization components. In some embodiments, thickness may also be measured using interferometry. Refractive index and absorption coefficient may be measured with interferometry. Absorption coefficient may also be measured with ellipsometry or reflectomery. In the case of an interferometer, off-axis interferograms present in surface data may be transformed to the Fourier space to obtain +1 and −1 diffraction orders. The diffraction orders may be band-pass filtered to calculate a spatial frequency representation of a complex electromagnetic field originating from a surface. Alternatively, a spatial frequency representation may also be obtained by Fourier transforming an on-axis interferogram. The spatial frequency representation is then inverse Fourier transformed to obtain the amplitude and phase of a complex electromagnetic field originating from the surface. Absorption coefficient may be measured from the amplitude of the electromagnetic field. Thickness and refractive index may be measured from the phase of the electromagnetic field. In the case of a wafer inspection system, haze may be measured by capturing scattered radiation from a surface region without feature. In some embodiments, correlation and deviation may be deduced from total integrated scatter from the surface. In the case of an atomic force microscope, correlation and deviation of surface roughness may be computed from high resolution images of a surface. For example, deviation is measured as the standard deviation of surface heights measured by an atomic force microscope. Correlation is measured as the width of the autocovariance of surface height image measured by the atomic force microscope.

In block 24, surface analytics is calculated using the surface properties computed from surface data and the prior information set available in the cloud. In some embodiments, the prior information set comprises surface properties from one or more surfaces and one or more batches. In some embodiments, the prior information set comprises a collection of tolerable values of surface properties. For example, in some embodiments, the prior information set comprises maximum and minimum tolerable values for multiple surface properties. In some embodiments, generating surface analytics comprises grouping of a subset of information in prior information set that correspond to one or more surface properties. In some embodiments, surface analytics comprises a trend of variation in one or more surface properties. For example, the number of features with sizes greater than a particular threshold may be computed from one or more surfaces in the prior information set. This information may then be compared with the number of features with sizes greater than the particular threshold in the case of the current surface under inspection. Accordingly, surface properties from a surface under inspection may be compared with surface properties from other reference surfaces. In some embodiments, the reference surfaces may be within the same batch as the surface under inspection. In some embodiments, the reference surfaces may be from a different batch from the surface under inspection.

In some embodiments, surface analytics comprises a list of surface properties that are likely to cause a negative impact in production yield. In such embodiments, generating surface analytics comprises comparing one or more surface properties with a list of tolerable values in the prior information set. The value of each surface property is compared with maximum and minimum tolerable value range. If the value is outside the minimum and maximum range established by the prior information set, then the surface property may be red flagged as a property that is likely to negatively affect production yield. Alternatively, a surface property may be marked as a harmless feature if the value of the surface property is within the established maximum and minimum tolerable values in the prior information set. Accordingly, useful analytical information such as variation trends in a surface property, and the yield-affecting capability of a surface property are computed using the surface properties calculated from surface data and the prior information set stored in the cloud.

In block 25, surface properties and surface analytics are transferred to the client using a communication pathway. Communication pathway refers to a channel through which client data is transferred to the client. In some embodiments, the cloud packetizes surface properties and surface analytics in accordance with the internet protocol suite. In some embodiments, the internet protocol suite comprises protocols operating in application layer, transport layer, internet layer, and link layer. The packetized data from cloud is sent from the application layer of the internet protocol suite to the transport layer, internet layer, and to the link layer. Each data packet comprises a destination address, which points to the client. Transmission from cloud may be accomplished with wired or wireless network interfaces on the client. In some embodiments, transmission control protocol is used in the transport layer. In other embodiments, user datagram protocol is used in the transport layer. In some embodiments, internet protocol is used in the internet layer. In some embodiments, real time streaming protocol is used in the application layer. In other embodiments, FTP is used in the application layer. In some embodiments, a twisted pair copper cable is used to physically transfer data from link layer. In some embodiments, an optical fiber is used to physically transfer data from link layer. In some embodiments, a coax cable is used to physically transfer data from link layer. In some embodiments, data is transferred wirelessly. For example, IEEE 802.11 protocol may be used to wirelessly communicate surface properties and surface analytics. In some embodiments, the communication pathway comprises routers that route surface data from cloud to the client.

The interconnected computing nodes present in cloud can be dynamically configured. In some embodiments, instances of a cloud application computing surface properties and surface analytics are executed in multiple computing nodes simultaneously. Accordingly, if one computing node fails due to hardware or software failures, the other interconnected computing nodes continue to compute surface properties and surface analytics. Furthermore, the other interconnected computing nodes recognize the failure of the failed computing node and automatically create a new computing node instance to compute surface properties and surface analytics. Therefore, computing on the cloud is reliable. Each computing node comprises processor, memory, and storage. The processing, memory, and storage capabilities can be scaled by increasing the number of computing nodes. Additionally, such a scaling upgrade may be performed elastically without the need for shutting down an inspection system. Accordingly, surface properties and surface analytics are generated with processing power, memory, and storage that are scalable, reliable, and upgradable on demand.

Figure 6:
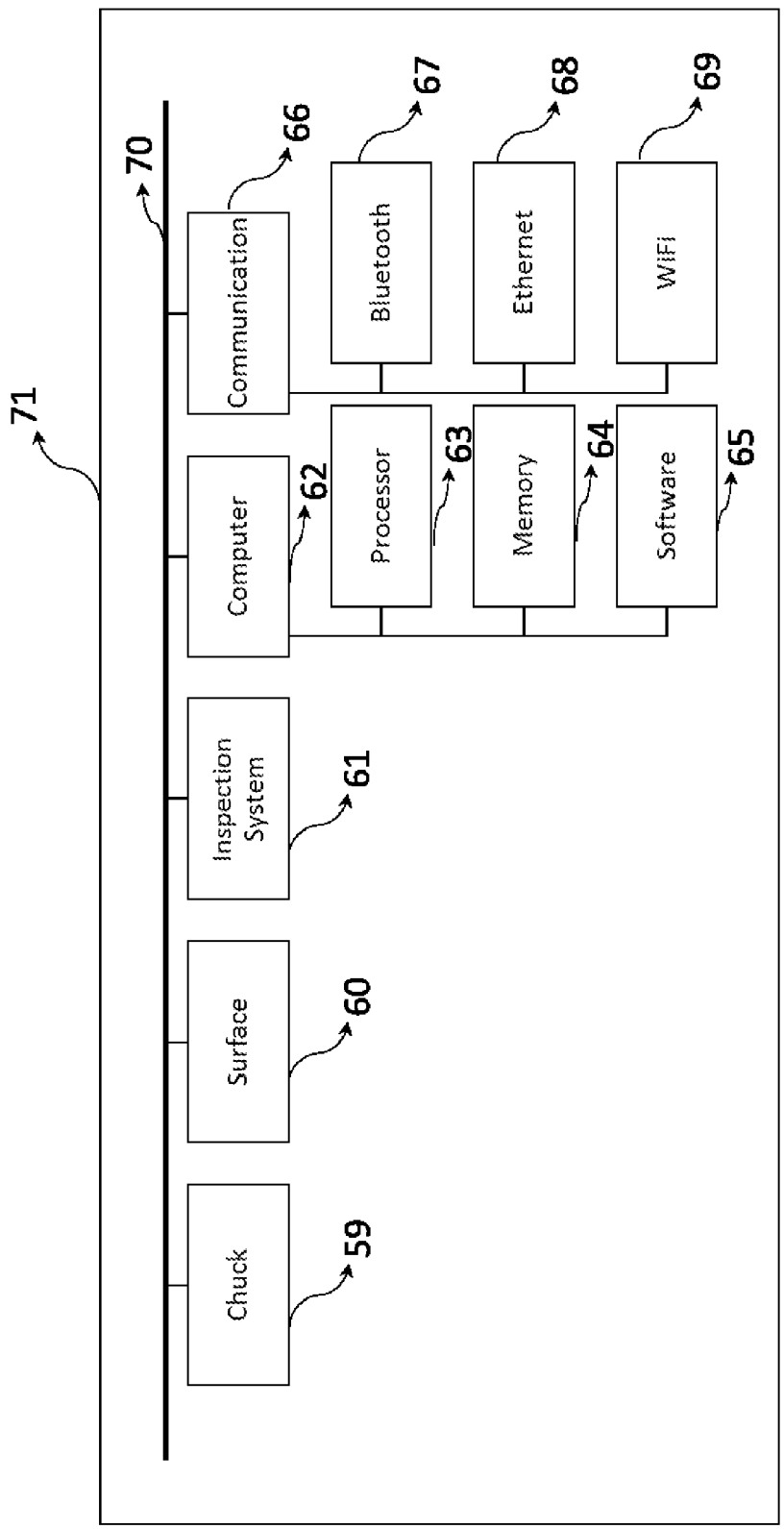
FIG. 6 shows a block diagram of an inspection system with cloud based processing, in accordance with the invention.

FIG. 6 shows a block diagram of an inspection system with cloud based processing, in accordance with the invention. A bus 70 connects various blocks of system 71, namely chuck 59, surface 60, inspection system 61, computer 62, and communication 66. Data and control signals are carried by bus 70. Chuck 59 includes an edge handling system that holds the edge of surface, vacuum system that holds the back side of surface with vacuum suction, gas vents, and support structures used to hold surface 60 flat. Surface 60 comprises the region to be inspected or measured by system 71. Surface 60 may be flat, curved due to gravity induced sag, or deformed due to coatings. Inspection system 61 generates surface data by inspecting surface 60. The surface data captured by inspection system 61 are transferred through bus 70 to computer 62. Inspection system 61 receives control information to adjust parameters such as exposure time and gain from computer 62 through bus 70. Computer 62 includes a processor 63, memory 64, and software 65. Computer 62 acts as the client that communicates with a cloud to transfer surface data to the cloud, and receive surface properties from the cloud. In some embodiments, the client also receives surface analytics from the cloud. In some embodiments, processor 63 compresses surface data. Software 65 generates control information and sends them through bus 70 to chuck 59, surface 60, and inspection system 61. Computer 62 connects to communication block 66 for communicating data and control information through bus 70. Communication block 66 includes Ethernet 68, WiFi 69, and Bluetooth 67.

Figure 7:
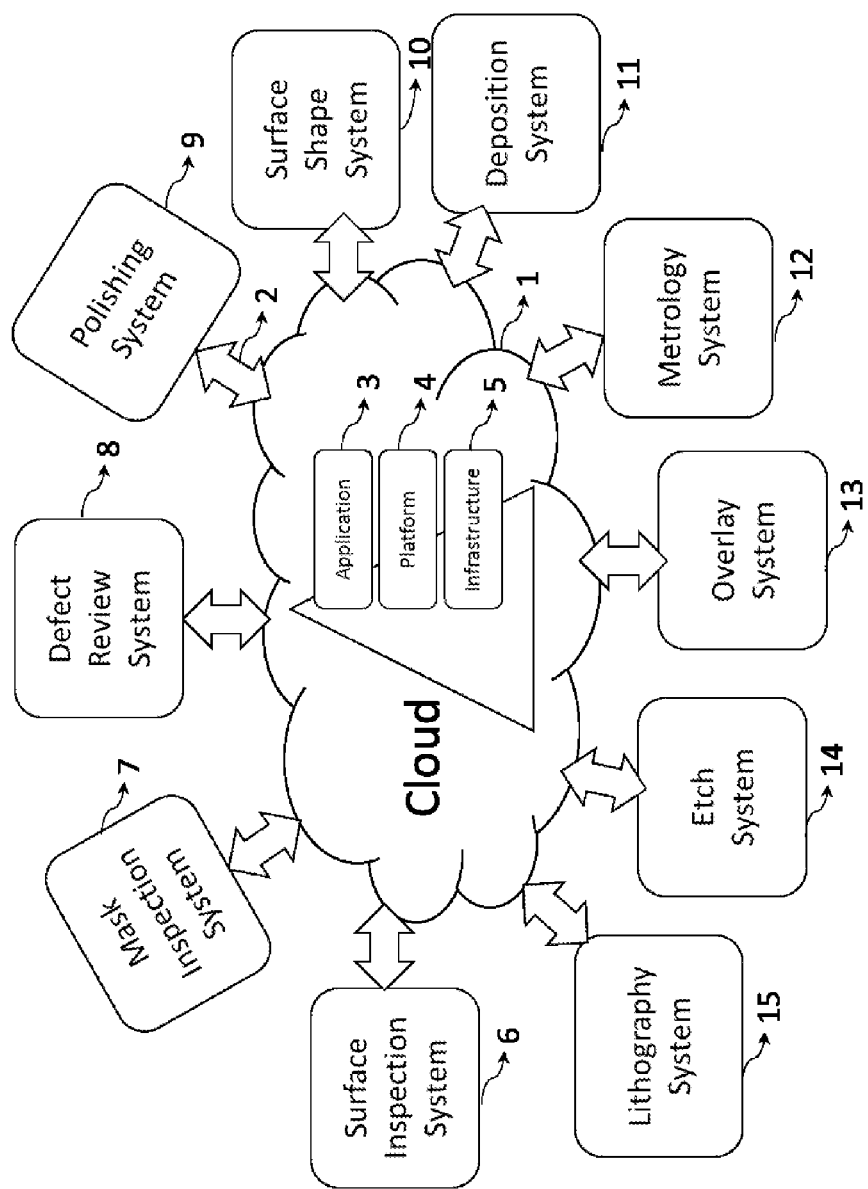
FIG. 7 depicts multiple process systems communicating with a cloud, in accordance with the invention.

FIG. 7 depicts multiple process systems communicating with a cloud, in accordance with the invention. One or more process systems that process a surface to produce an article are connected to a cloud. In some embodiments, process systems are semiconductor capital equipment systems. In some embodiments, the articles are ICs. Process systems include surface inspection system 6, mask inspection system 7, defect review system 8, polishing system 9, surface shape system 10, deposition system 11, metrology system 12, overlay system 13, etch system 14, and lithography system 15. Cloud 1 comprises an interconnected network of computing nodes. In some embodiments, cloud 1 comprises an infrastructure layer 5, a platform layer 4, and an application layer 3. The infrastructure layer 5 comprises processors, memory, storage, and network interfaces. The application layer 3 comprises software applications. In some embodiments, the software applications on the application layer 3 generates root cause list comprising a list of process information responsible for the failure of an article, such as an IC. In some embodiments, the software applications on the application layer 3 generate surface properties from surface data. In some embodiments, the software applications on the application layer 3 generates surface analytics from surface properties. The platform layer 4 comprises software such as operating system, database, and development systems that facilitate the operation of applications in the application layer 3 on the infrastructure layer 5. In some embodiments, the software applications on the application layer 3 may be deployed as a software as a service model. In other applications, the platform layer 4 may be deployed as a platform as a service model. In some embodiments, the infrastructure layer 5 may be deployed as an infrastructure as a service model. In some embodiments, cloud 1 is a private cloud, which is dedicated to one or more semiconductor fabs. In other embodiments, cloud 1 is a public cloud, which is shared between multiple diverse cloud users. In some embodiments, cloud 1 is a hybrid cloud, comprising interconnected private and public clouds.

In some embodiments, process systems transfer process data to cloud 1 through a communication pathway 2. Process data from a process system includes surface data captured from a surface. Further, process data also comprises setup parameters of the process system. Surface data refers to data that is used to compute surface properties comprising information of features and information on layer. Set up parameters refer to configuration data of the process system, including recipes, used for processing the surface.

In other embodiments, process systems transfer process information to cloud 1 through a communication pathway 2. Process information from a process system includes surface properties comprising information of features and information on layer. Further, process information also comprises setup parameters of the process system. Set up parameters refer to configuration data of the process system, including recipes, used for processing the surface.

In some embodiments, a process system comprises a client to communicate with the cloud. In some embodiments, process systems include clients dedicated for root cause analysis of failures. Such clients are called as root cause clients. In some embodiments, the client compresses process data or process information before transmitting it to the cloud. In some embodiments, the client packetizes process data or process information according to the internet protocol suite. The process data or process information from client is transferred to the cloud using a communication pathway. Communication pathway refers to a channel through which process data or process information is communicated to the cloud. The packetized process data or process information from client is sent from the application layer of the internet protocol suite to the transport layer, internet layer, and to the link layer. Each data packet comprises a destination address, which points to the cloud. Transmission from client may be accomplished with wired or wireless network interfaces on the client. In some embodiments, transmission control protocol is used in the transport layer. In other embodiments, user datagram protocol is used in the transport layer. In some embodiments, internet protocol is used in the internet layer. In some embodiments, real time streaming protocol is used in the application layer. In other embodiments, FTP is used in the application layer. In some embodiments, a twisted pair copper cable is used to physically transfer data from link layer. In some embodiments, an optical fiber is used to physically transfer data from link layer. In some embodiments, a coax cable is used to physically transfer data from link layer. In some embodiments, data is transferred wirelessly. For example, IEEE 802.11 protocol may be used to wirelessly communicate process data or process information. In some embodiments, the communication pathway comprises routers that route process data or process information from client to the cloud.

In some embodiments, process information is computed in the cloud from process data transferred from a client to the cloud, with the client connected to a process system generating process data. In some embodiments, surface properties (comprised in process information) is transferred to process systems using the communication path way. In other embodiments, process information is transferred from process systems to cloud. That is, in such embodiments, process information is transferred from a client to cloud, with the client connected to a process system generating process information. A root cause list comprising process information responsible for failure of an article, such as an IC, is generated in the cloud. In some embodiments, surface analytics is transferred to process systems using the communication path way. In some embodiments, the root cause list is transferred to the root cause client using the communication path way. In some embodiments, data transmitted from cloud to client is compressed before transmission. In some embodiments, the cloud packetizes the data to be transmitted according to the internet protocol suite. In some embodiments, the internet protocol suite comprises protocols operating in application layer, transport layer, internet layer, and a link layer. The packetized data from cloud is sent from the application layer of the internet protocol suite to the transport layer, internet layer, and to the link layer. Each data packet comprises a destination address, which points to the client. Transmission from cloud may be accomplished with wired or wireless network interfaces on the client. In some embodiments, transmission control protocol is used in the transport layer. In other embodiments, user datagram protocol is used in the transport layer. In some embodiments, internet protocol is used in the internet layer. In some embodiments, real time streaming protocol is used in the application layer. In other embodiments, FTP is used in the application layer. In some embodiments, a twisted pair copper cable is used to physically transfer data from link layer. In some embodiments, an optical fiber is used to physically transfer data from link layer. In some embodiments, a coax cable is used to physically transfer data from link layer. In some embodiments, data is transferred wirelessly. For example, IEEE 802.11 protocol may be used to wirelessly communicate data from cloud to a client. In some embodiments, the communication pathway comprises routers that route data from cloud to the client.

The interconnected computing nodes present in cloud can be dynamically configured. In some embodiments, instances of a cloud application computing surface properties and surface analytics are executed in multiple computing nodes simultaneously. Similarly, in some embodiments, instances of a cloud application computing root cause list are executed in multiple computing nodes simultaneously. Accordingly, if one computing node fails due to hardware or software failures, the other interconnected computing nodes continue with their computations. Furthermore, the other interconnected computing nodes recognize the failure of the failed computing node and automatically create a new computing node instance to compensate for the failed computing node. Therefore, computing on the cloud is reliable. Each computing node comprises processor, memory, and storage. The processing, memory, and storage capabilities can be scaled by increasing the number of computing nodes. Additionally, such a scaling upgrade may be performed elastically without the need for shutting down an inspection system. Accordingly, root causes of failures are analytically determined with processing power, memory, and storage that are scalable, reliable, and upgradable on demand.

Figure 8:
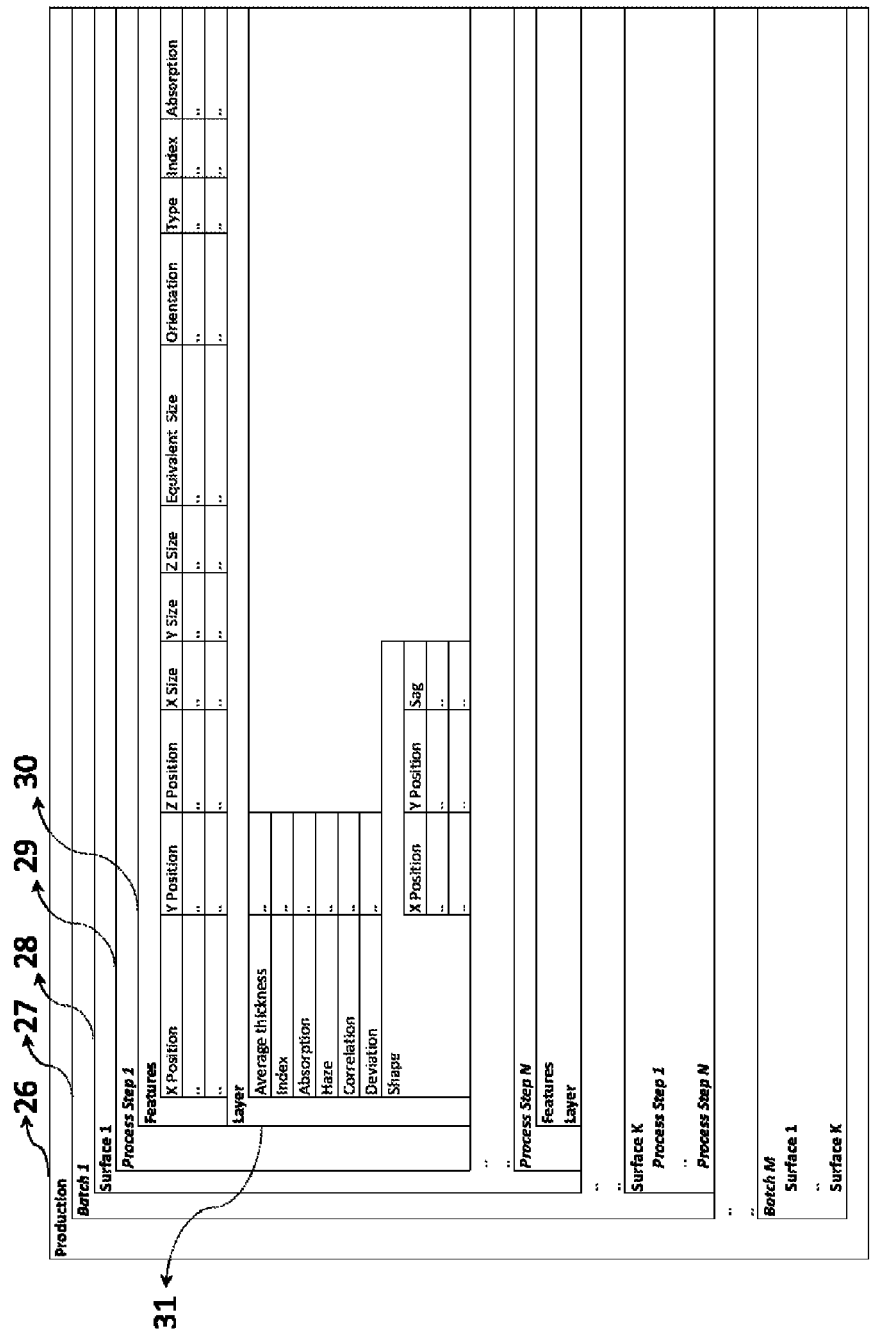
FIG. 8 illustrates process information from multiple batches, with each batch comprising multiple surfaces, and each surface comprising multiple process steps, in accordance with the invention.

FIG. 8 illustrates process information from multiple batches, with each batch comprising multiple surfaces, and each surface comprising multiple process steps, in accordance with the invention. Fabrication of an article, such as an IC, comprises multiple process steps. In some embodiments, process information from each significant process step 29 is stored in the cloud. Process information includes information on features 30 and information on layer 31. A surface undergoes multiple process steps, and process information is generated after each process step. Accordingly, in some embodiments, process information of a surface 28 comprises process information from multiple process steps. In some embodiments, a batch comprises multiple surfaces. Accordingly, process information for a batch 27 comprises process information from multiple surfaces. In some embodiments, production comprises multiple batches. Accordingly, process information for production 26 comprises process information from multiple batches. The process information of production 26 is accumulated in the cloud from process systems that process multiple batches, with each batch comprising multiple surfaces, and with each surface undergoing multiple process steps. In some embodiments process information of production 26 is stored in a database located in the cloud.

Figure 9:
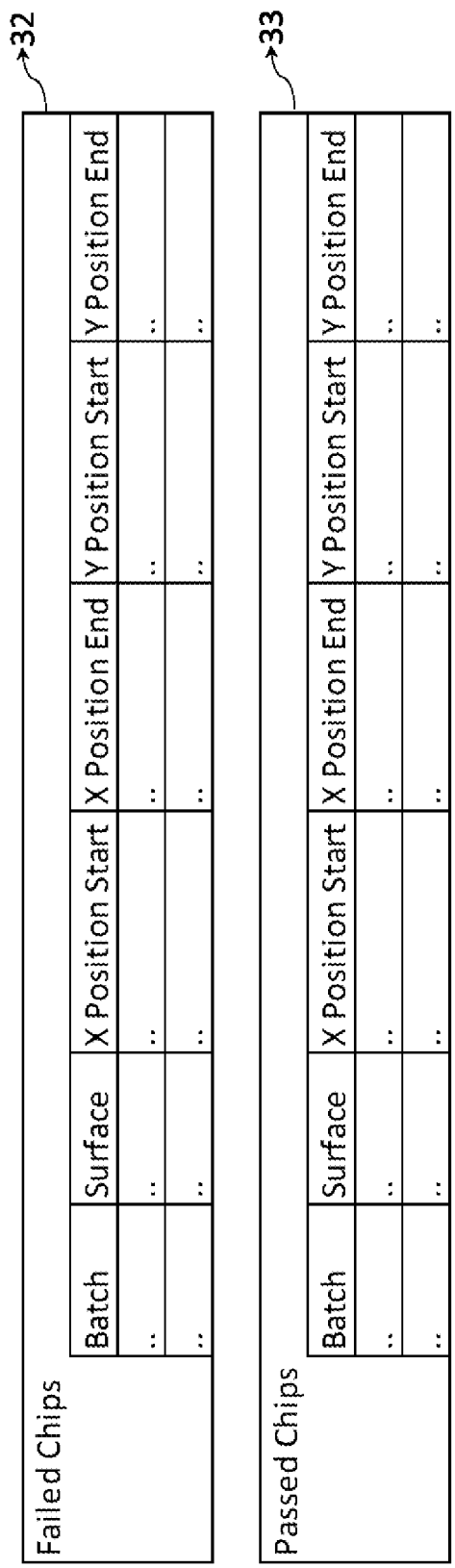
FIG. 9 illustrates functional results comprising identifying information of articles that have failed a functional test and identifying information of said articles that have passed the functional test, in accordance with the invention.

FIG. 9 illustrates functional results comprising identifying information of articles that have failed a functional test and identifying information of articles that have passed the functional test, in accordance with the invention. Functional test refers to examining the functionality of a produced article, such as an IC. In some embodiments, functional tests are performed at the end of fabrication after a surface undergoes all process steps. In other embodiments, functional tests are performed before the end of all process steps. The result of a functional test identifies ICs that have failed the functional test 32 and ICs that have passed the functional test 33. In some embodiments, identifying information includes batch ID, surface ID, X position start, X position end, Y position start, and Y position end. Batch ID refers to a unique identity information for a batch. Similarly, surface ID refers to a unique identity information for a surface. X position start and X position end refers to start and end points, respectively, of the location of an IC along the X dimension. Similarly, Y position start and Y position end refers to the start and end points, respectively, of the location of an IC along the Y dimension. In some embodiments, identifying information comprises other ways of identifying an IC. For example, identifying information may include the position of midpoint of an IC. The identifying information shown in 32 and 33 are exemplary. In some cases, additional information, such as midpoint and size of IC, may be included. In other cases, identifying information may only comprise surface ID and a position of an IC. In some embodiments, surface ID refers to wafer ID printed on a surface.

Figure 10:
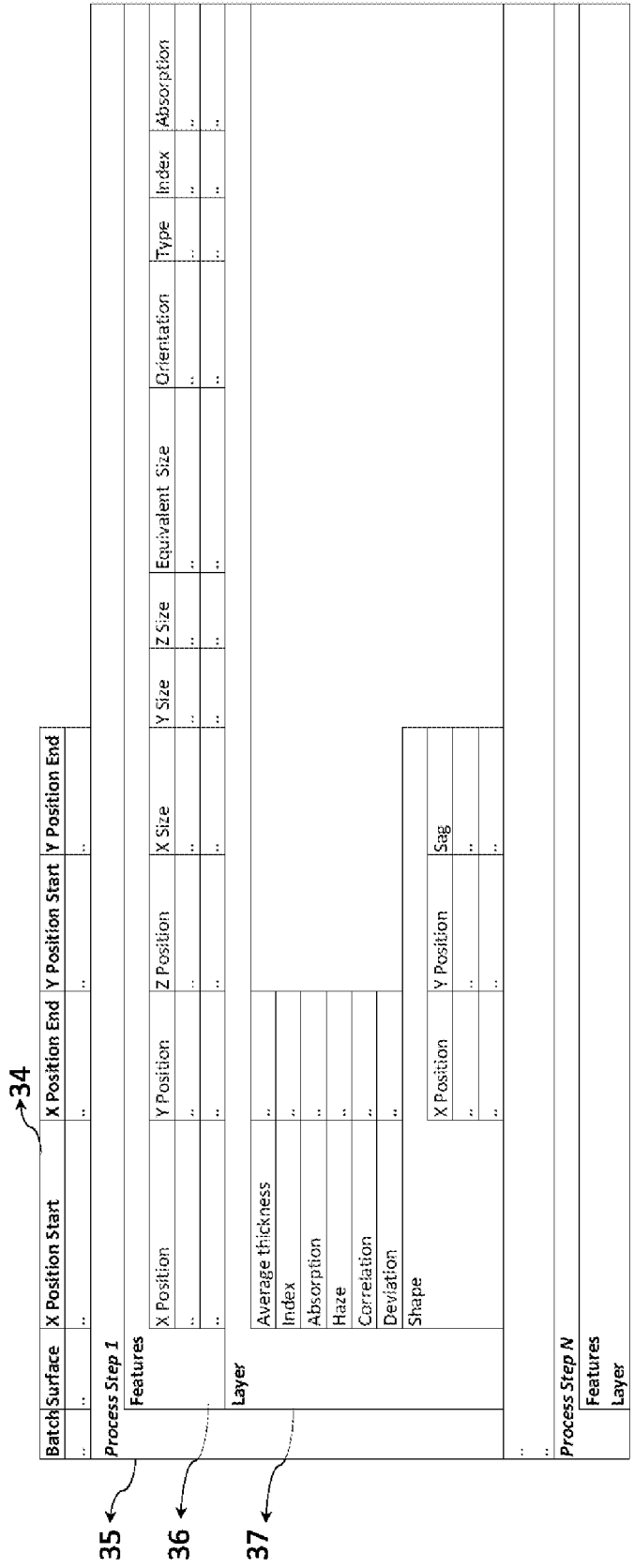
FIG. 10 illustrates process information comprising multiple process steps corresponding to a surface listed in functional results, in accordance with the invention.

FIG. 10 illustrates process information comprising multiple process steps corresponding to a surface listed in functional results, in accordance with the invention. The process information of a failed or a passed IC is retrieved using the identifying information 34 obtained from functional results. For instance, batch ID is used to identify the batch; surface ID is used to identify a surface within the batch; and X position start, X position end, Y position start, and Y position end are used to identify the spatial region within the surface where the IC is located. The process information corresponding to the location of a failed or a passed IC are retrieved from the production process information illustrated in FIG. 8. The retrieved process information corresponding to the location of an IC comprises process information from one or more process steps. Process information for each process step 35 comprises surface information, and process configuration parameters obtained from process systems. Surface information includes information on features 36 and information on layer 37.

In some embodiments, functional results comprise failed ICs. It becomes important to identify the root cause of failures, so as to eliminate them in an effort to maximize production yield. Since fabricating an article, such as an IC, comprises multiple exhaustive complex process steps, root cause of failure may lie in any of the process steps. Additionally, each process step has multiple process information. The root cause of failure may lie in one or more process information of a one or more process steps.

Figure 11:
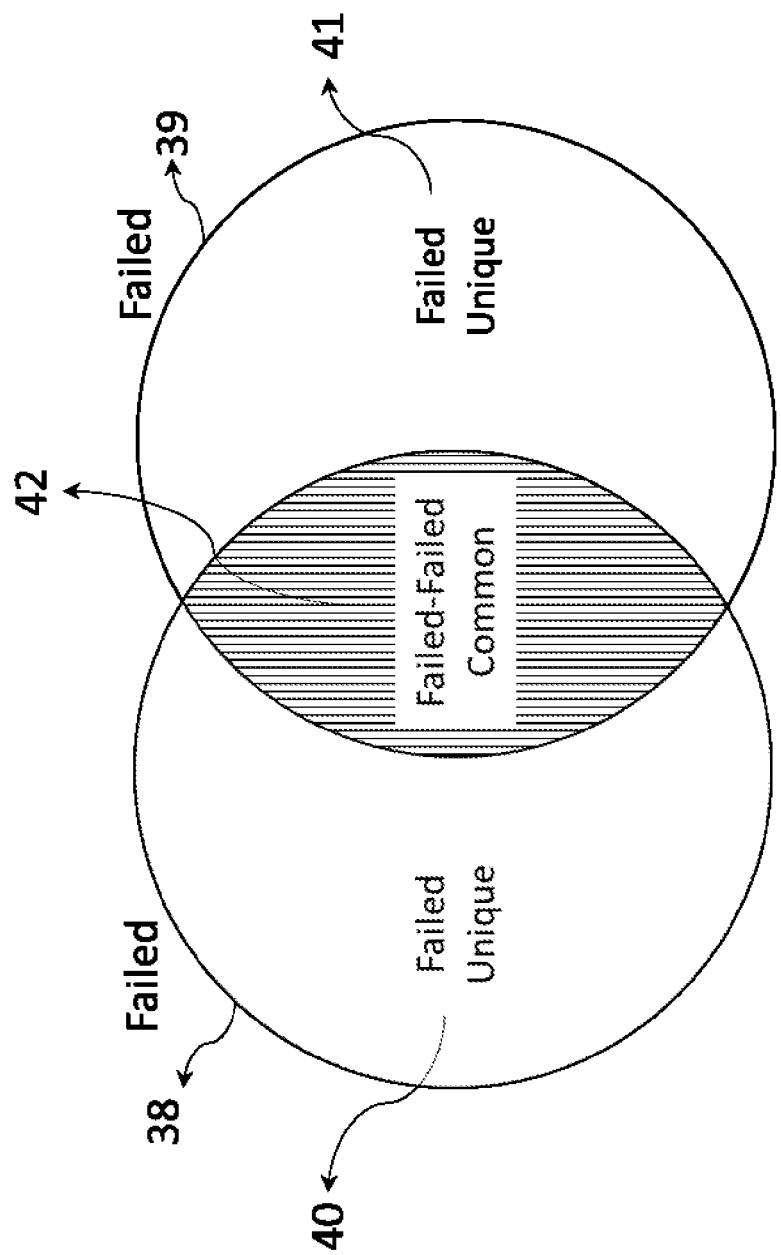
FIG. 11 depicts an exemplary Venn diagram highlighting similarities between the process information of two or more said failed articles, in accordance with the invention.

FIG. 11 depicts an exemplary Venn diagram highlighting similarities between the process information of two or more failed articles, in accordance with the invention. In some embodiments, process information responsible for failure of an IC may be short-listed by finding similarities between process information of failed ICs. This is illustrated with a Venn diagram comprising process information of a first failed IC 38 and process information of a second failed IC 39. Failed Unique 40 represents process information that is unique to first failed IC. Failed Unique 41 represents process information that is unique to second failed IC. Failed-Failed Common 42 represents process information that is common to the process information of first and second failed ICs. For example, consider two ICs, A and B, that have failed a functional test. Failed Unique for IC A and IC B comprises position information of features in various process steps. The position information is included in Failed Unique because the position information of features have different values in A and B. Failed-Failed Common for ICs A and B comprise feature size and layer thickness information for a particular process step. Feature size information is included in Failed-Failed Common because feature size values are similar between A and B. Similarly, layer thickness information is included in Failed-Failed Common because layer thickness values are similar between A and B.

Figure 12:
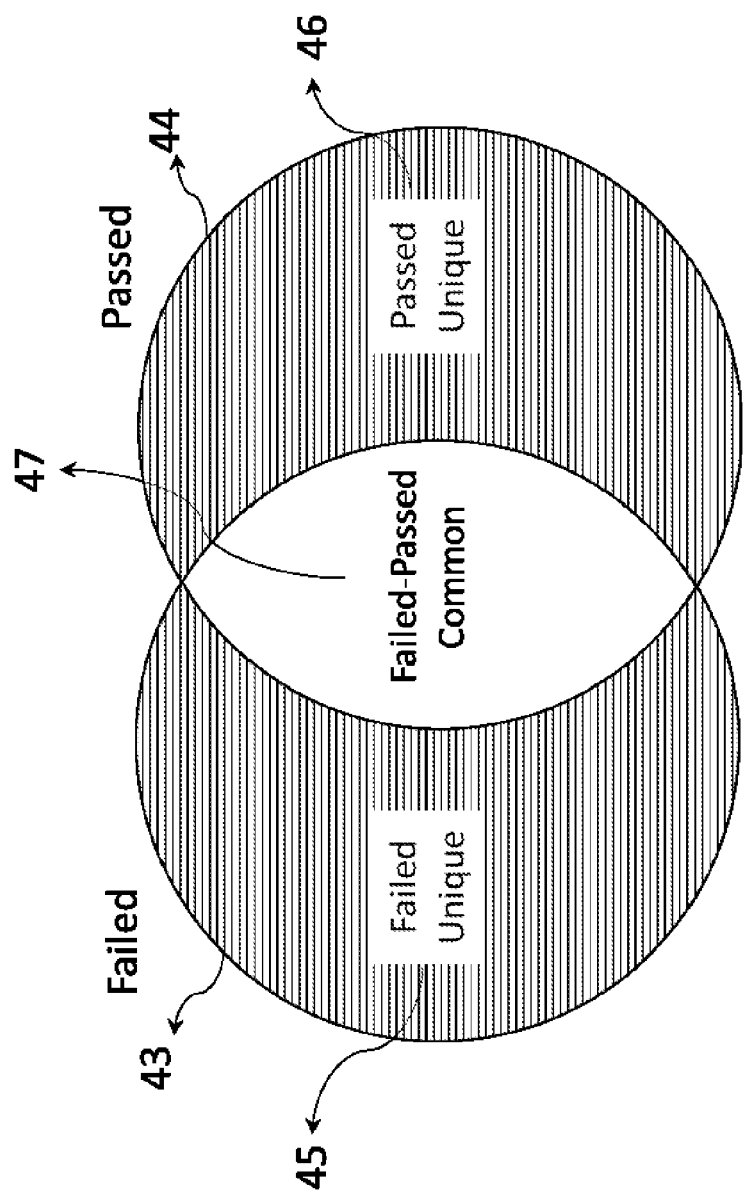
FIG. 12 depicts an exemplary Venn diagram highlighting differences between process information of a failed article and process information of a passed article, in accordance with the invention.

FIG. 12 depicts an exemplary Venn diagram highlighting differences between process information of a failed article and process information of a passed article, in accordance with the invention. In some embodiments, process information responsible for failure of an IC may be short-listed by finding differences between process information of a failed IC and a passed IC. This can be illustrated with a Venn diagram comprising process information of a failed IC 43 and process information of a passed IC 44. Failed Unique 45 represents process information that is unique to the failed IC. Passed Unique 41 represents process information that is unique to the passed IC. Failed-Passed Common 47 represents process information that is common to the process information of the failed IC and process information of the passed IC. For example, consider the IC A that has failed the functional test and an IC D has passed the functional test. Failed Unique for A and Passed Unique for D comprises position and size information of features in various process steps. The position information are included in Failed Unique and Passed Unique because the position information of features have different values in A and D. Similarly, size information is included in Failed Unique and Passed Unique because the size information of features have different values in A and D. Failed-Passed Common for ICs A and D comprises layer thickness information for a particular process step. Layer thickness information is included in Failed-Passed Common because layer thickness values are similar between A and D.

Figure 13:
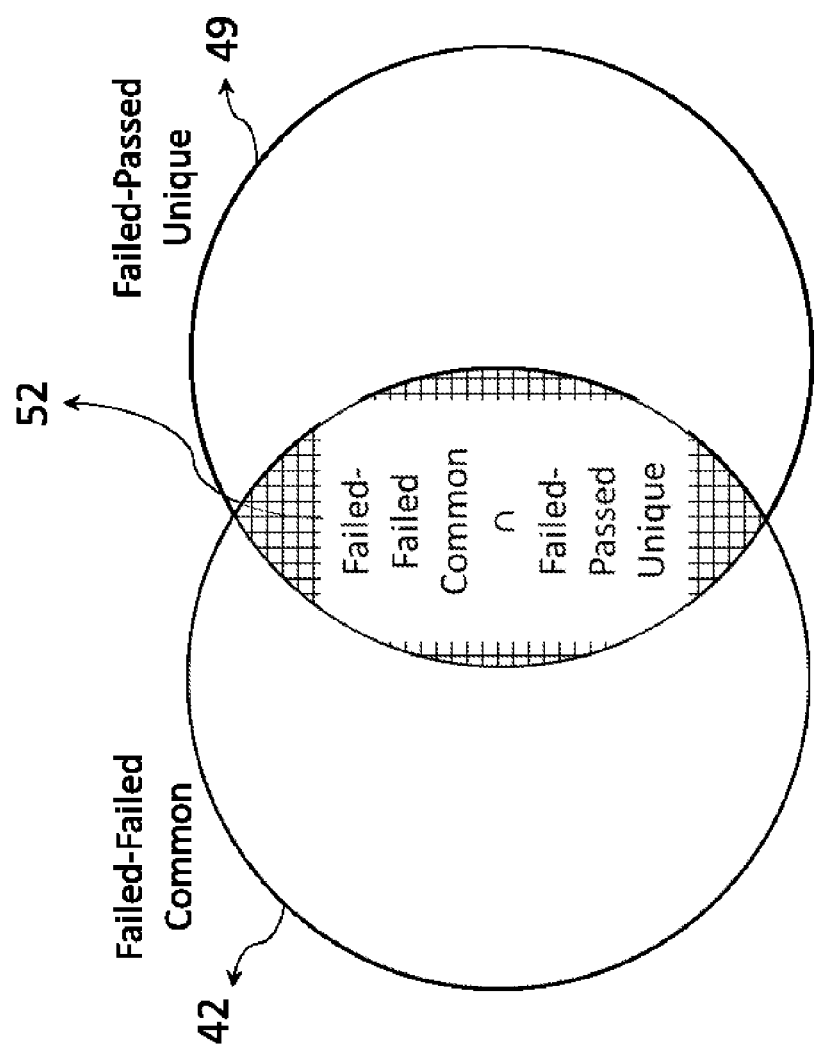
FIG. 13 depicts an exemplary Venn diagram highlighting similarities between Failed-Failed Common and Failed-Passed Unique, in accordance with the invention.

FIG. 13 depicts an exemplary Venn diagram highlighting similarities between Failed-Failed Common and Failed-Passed Unique, in accordance with the invention. Failed-Failed Common 48 refers to a set of similarities between process information of two failed ICs. Failed-Passed Unique 49 refers to the union of Failed Unique and Passed Unique. Failed Unique refers to process information of a failed IC that is not common with process information of a passed IC. Passed Unique refers to process information of a passed IC that is not common with process information of a failed IC. In some embodiments, the intersection 52 of Failed-Failed Common and Failed-Passed Unique is considered as the process information responsible for failure. In other words, root cause of failure is found by finding the similarities between a) similarities of failed defects and b) differences between failed as passed defects. Root cause of failure refers to process information that is responsible for the failure of an IC.

For example, consider two ICs, A and B, that have failed a functional test. Failed Unique for IC A and IC B comprises position information of features in various process steps. The position information is included in Failed Unique because the position information of features have different values in A and B. Failed-Failed Common for ICs A and B comprise feature size and layer thickness information for a particular process step. Feature size information is included in Failed-Failed Common because feature size values are similar between A and B. Similarly, layer thickness information is included in Failed-Failed Common because layer thickness values are similar between A and B. Also, consider an IC D that has passed the functional test. Failed Unique for A and Passed Unique for D comprises position and size information of features in various process steps. The position information for a particular process step are included in Failed Unique and Passed Unique because the position information of features have different values in A and D. Similarly, size information is included in Failed Unique and Passed Unique because the size information of features have different values in A and D. Failed-Passed Common for ICs A and D comprises layer thickness information for a particular process step. Layer thickness information is included in Failed-passed common because layer thickness values are similar between A and D. Failed-Passed Unique for A and D comprises position and size information of features. The intersection of Failed-Failed Common and Failed-Passed Unique comprises feature size information for a particular process step. Accordingly, the root cause of defect failure is analytically determined as the size of features in a particular process step.

Figure 14:
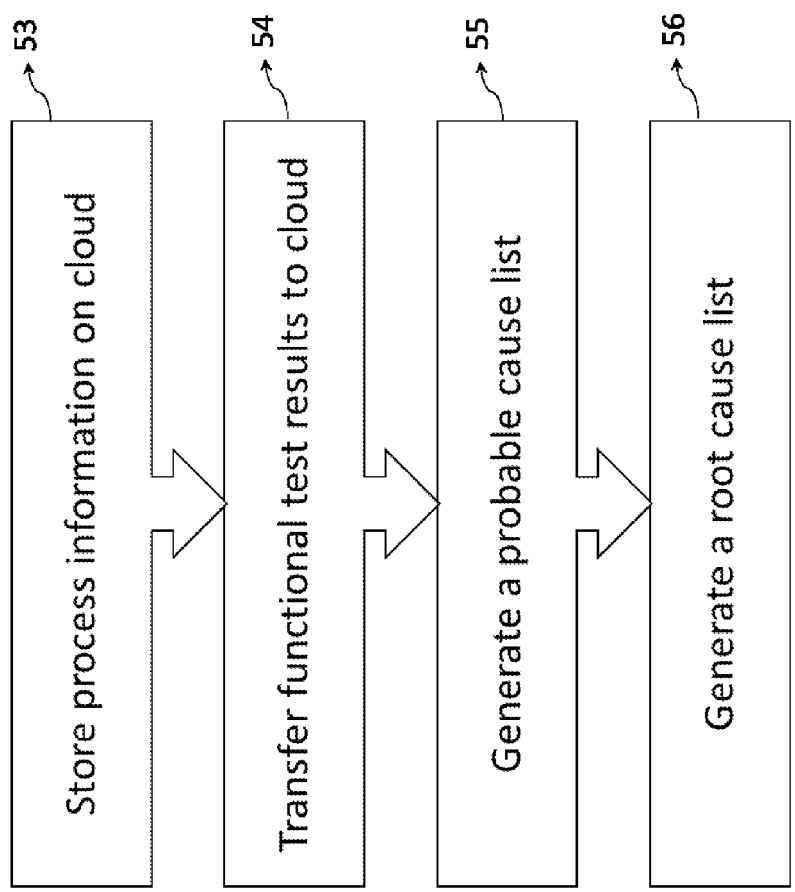
FIG. 14 illustrates an exemplary flow chart for improving production yield of an article by generating a root cause list comprising process information responsible for failure in failed articles, in accordance with the invention.

FIG. 14 illustrates an exemplary flow chart for improving production yield of an article by generating a root cause list comprising process information responsible for failure in failed articles, in accordance with the invention. In some embodiments, process data from client is transferred to the cloud using a communication pathway. In other embodiments, process information from client is transferred to the cloud using a communication pathway. Communication pathway refers to a channel through which client data is communicated to the cloud. In some embodiments, the process data or process information is compressed to minimize data size. In some embodiments, the client packetizes process data or process information. The packetized data from client is sent from the application layer of the internet protocol suite to the transport layer, internet layer, and to the link layer. Each data packet comprises a destination address, which points to the cloud. Transmission from client may be accomplished with wired or wireless network interfaces on the client. In some embodiments, transmission control protocol is used in the transport layer. In other embodiments, user datagram protocol is used in the transport layer. In some embodiments, internet protocol is used in the internet layer. In some embodiments, real time streaming protocol is used in the application layer. In other embodiments, FTP is used in the application layer. In some embodiments, a twisted pair copper cable is used to physically transfer data from link layer. In some embodiments, an optical fiber is used to physically transfer data from link layer. In some embodiments, a coax cable is used to physically transfer data from link layer. In some embodiments, data is transferred wirelessly. For example, IEEE 802.11 protocol may be used to wirelessly communicate process data or process information. In some embodiments, the communication pathway comprises routers that route process data or process information from client to the cloud. In embodiments where process data is communicated from client to cloud, process information is computed from process data in the cloud.

In block 53, process information is stored in the cloud. In some embodiments, process information comprises characteristic data about a constituent of an article. In some embodiments, process information comprises parameters of a process step used in fabrication of the article. For example, process information comprises information on features, information on layer, and configuration parameters of process systems. Process information is stored for one or more process steps. A surface undergoes multiple process steps. A batch comprises one or more surfaces. And there are multiple batches in production. Accordingly, in some embodiments, process information corresponding to one or more process steps of one or more surfaces in one or more batches is stored. This collection of process information is called a process information repository.

In block 54, functional test results are transferred to the cloud. Functional test results comprise identifying information about failed and passed articles. Identifying information include batch ID, surface ID, and spatial position information of an article. In some embodiments, functional test results are transferred to the cloud from a client. In some embodiments, functional test results are compressed before transmission from client to cloud. In such embodiments, the cloud decompresses the functional test results. In some embodiments, the client packetizes the functional test results in accordance with the internet protocol suite.

In block 55, a probable cause list is generated from process information repository and functional test results. The probable cause list comprises process information that are responsible for failure of an article, such as an IC. In some embodiments, the probable cause list may also comprise process information that are not responsible for failure of an article. In such embodiments, the probable cause list comprises process information that are responsible for article failure and process information that are not responsible for article failure. Nevertheless, the process information in probable cause list is a substantially short-listed version of the process information repository. The probable cause list is generated by finding the differences between the process information of a passed article and the process information of a failed article. Accordingly, process information that are common to both passed and failed articles are not included in the probable cause list.

In block 56, a root cause list is generated using the probable cause list. In some embodiments, the root cause list is generated using the probable cause list and the process information repository. The root cause list comprises process information that are responsible for failure of an article, such as an IC. In some embodiments, the root cause list is a short-listed version of the probable cause list. In some embodiments, root cause list is the same as the probable cause list. In some embodiments, the root cause list is generated by finding the similarities between probable cause list and a list of similarities comprising similarities between the process information of two or more failed articles. That is, similarities between process information of failed articles are first determined. The root cause list is then computed as the common process information between the probable cause list and similarities between process information of failed articles. Accordingly, in some embodiments, the root-cause list comprises process information that are responsible for failure of an article. In some embodiments, the root cause list is transferred from the cloud to a client.

With the knowledge of root cause of article failures, process steps can be readily modified to contain the propagation of abnormalities and defects, leading to a minimization of negative impact on yield. This effectively results in a maximization of production yield. In addition to monitoring yield in production, such an analytical root cause analysis may also be used in development phase to design flawless recipes for each process step in the fabrication of an article, such as an IC.

The interconnected computing nodes present in cloud can be dynamically configured. In some embodiments, instances of a cloud application computing surface properties and surface analytics are executed in multiple computing nodes simultaneously. Similarly, in some embodiments, instances of a cloud application computing root cause list are executed in multiple computing nodes simultaneously. Accordingly, if one computing node fails due to hardware or software failures, the other interconnected computing nodes continue with their computations. Furthermore, the other interconnected computing nodes recognize the failure of the failed computing node and automatically create a new computing node instance to compensate for the failed computing node. Therefore, computing on the cloud is reliable. Each computing node comprises processor, memory, and storage. The processing, memory, and storage capabilities can be scaled by increasing the number of computing nodes. Additionally, such a scaling upgrade may be performed elastically without the need for shutting down an inspection system. Accordingly, root causes of failures are analytically determined with processing power, memory, and storage that are scalable, reliable, and upgradable on demand.

It will be recognized by those skilled in the art that various modifications may be made to the illustrated and other embodiments of the invention described above, without departing from the broad inventive scope thereof. It will be understood therefore that the invention is not limited to the particular embodiments or arrangements disclosed, but is rather intended to cover any changes, adaptations or modifications which are within the scope and spirit of the invention as defined by the appended claims.

It should be understood that the present invention as described above can be implemented in the form of control logic using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described above, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

In the claims, reference to an element in the singular is not intended to mean "one and only one" unless explicitly stated, but rather is meant to mean "one or more." In addition, it is not necessary for a device or method to address every problem that is solvable by different embodiments of the invention in order to be encompassed by the claims.

The above description is illustrative and is not restrictive. Many variations of the disclosure will become apparent to those skilled in the art upon review of the disclosure. The scope of the disclosure should, therefore, be determined not with reference to the above description, but instead should be determined with reference to the pending claims along with their full scope or equivalents.

One or more features from any embodiment may be combined with one or more features of any other embodiment without departing from the scope of the disclosure. Further, modifications, additions, or omissions may be made to any embodiment without departing from the scope of the disclosure. The components of any embodiment may be integrated or separated according to particular needs without departing from the scope of the disclosure.

What is claimed is:

1. A system for inspecting a surface with cloud based processing, comprising:

an inspection module to generate surface data by inspecting a surface;

a client connected to said inspection module having a processor configured to:
- compress the size of said surface data to generate compressed surface data;
- packetize said compressed surface data to generate packetized surface data;

a bidirectional communication pathway configured to:
i. transfer said packetized surface data from said client to a cloud, wherein said cloud comprises multiple interconnected computing nodes that are remotely located from said client;
ii. transfer surface properties and surface analytics from said cloud to said client; and a processor located in said cloud configured to:
- reconstruct said packetized surface data to generate said compressed surface data;
- decompress the size of said compressed surface data to generate said surface data;
i. compute said surface properties using said surface data;
ii. compute said surface analytics from said surface properties and a prior information set, wherein said prior information set is a collection of surface properties, previously stored in said cloud, obtained by inspecting at least two surfaces, whereby said surface properties and said surface analytics are reliably used to improve the yield of an article produced with said surface.

2. The system of claim 1, wherein said surface data is stored in said cloud.

3. The system of claim 1, wherein said surface data comprises a digital representation of an electromagnetic radiation scattered from said surface.

4. The system of claim 1, wherein said surface properties comprise position and size of features located on said surface.

5. The system of claim 1, wherein said surface properties comprise shape and thickness.

6. The system of claim 1, wherein said surface analytics comprises a trend of variation in one or more surface properties.

7. The system of claim 1, wherein said surface analytics comprises a list of said surface properties that are likely to cause a negative impact on production yield.

8. The system of claim 1, wherein said cloud is a private cloud.

9. The system of claim 1, wherein said cloud is a hybrid cloud.

10. The system of claim 1, wherein said cloud is a public cloud.

11. The system of claim 1, wherein said packetized surface data is generated according to the internet protocol suite.

12. The system of claim 1, further comprising a processor in cloud configured to generate packets comprising said surface properties and said surface analytics according to the internet protocol suite.

13. The system of claim 1, wherein said communication pathway comprises an optical fiber.

14. The system of claim 1, wherein said communication pathway comprises a twisted pair copper cable.

15. The system of claim 1, wherein said communication pathway comprises a wireless router.

16. The system of claim 1, wherein said communication pathway comprises a coax cable.

17. A method for inspecting a surface with cloud based processing, comprising:

generating surface data by inspecting a surface with an inspection module, wherein said inspection module is connected to a client;

compressing the size of said surface data in said client to generate compressed surface data;

packetizing said compressed surface data in said client to generate packetized surface data;

transferring said packetized surface data from said client to a cloud, wherein said cloud comprises multiple interconnected computing nodes that are remotely located from said client;

reconstructing said packetized surface data in said cloud to generate said compressed surface data;

decompressing the size of said compressed surface data in said cloud to generate said surface data;

computing surface properties using said surface data on said cloud;

computing surface analytics in said cloud from said surface properties and a prior information set, wherein said prior information set is a collection of surface properties, previously stored in said cloud, obtained by inspecting at least two surfaces; and transferring said surface properties and said surface analytics from said cloud to said client, whereby said surface properties and said surface analytics are reliably used to improve the yield of an article produced with said surface.

18. The method of claim 17, wherein said generating surface analytics comprises grouping of a subset of information in said prior information set that correspond to one or more surface properties.

19. The method of claim 17, wherein said prior information set further comprises a collection of tolerable values of surface properties.

20. The method of claim 19, wherein said generating surface analytics comprises comparing one or more said surface properties with said tolerable values.

* * * * *